(12) United States Patent
Engelbart et al.

(10) Patent No.: US 7,562,593 B2
(45) Date of Patent: Jul. 21, 2009

(54) APPARATUS AND METHODS FOR ADJUSTABLY SUPPORTING PROBES

(75) Inventors: Roger W. Engelbart, St. Louis, MO (US); Eugene A. Myers, St. Charles, MO (US); Nancy L. Wood, Clayton, MO (US)

(73) Assignee: The Boeing Company, Chicago, IL (US)

( * ) Notice: Subject to any disclaimer, the term of this patent is extended or adjusted under 35 U.S.C. 154(b) by 466 days.

(21) Appl. No.: 11/609,235

(22) Filed: Dec. 11, 2006

(65) Prior Publication Data

US 2007/0079662 A1    Apr. 12, 2007

Related U.S. Application Data

(63) Continuation-in-part of application No. 11/183,203, filed on Oct. 6, 2005, now abandoned.

(51) Int. Cl.
*G01D 21/00* (2006.01)
(52) U.S. Cl. ...................................... 73/866.5
(58) Field of Classification Search ............ 73/104, 73/105, 681, 620–623, 866.5, 865.8, 150 R; 324/228, 229, 334
See application file for complete search history.

(56) References Cited

U.S. PATENT DOCUMENTS

| | | |
|---|---|---|
| 2,537,731 A | 1/1951 | Angell |
| 3,931,570 A | 1/1976 | George et al. |
| 4,170,145 A | 10/1979 | Kennedy et al. |
| 4,510,693 A | 4/1985 | Cusack |
| 4,547,971 A | 10/1985 | Imazeki |
| 4,763,421 A | 8/1988 | Feichtinger |
| 4,859,817 A | 8/1989 | Cassani |
| 5,024,003 A | 6/1991 | Breyer |
| 5,051,933 A | 9/1991 | Sarr et al. |
| 5,151,652 A | 9/1992 | Moschuering |
| 5,299,361 A | 4/1994 | Fiedler |
| 5,323,540 A | 6/1994 | McMurtry et al. |
| 5,435,072 A | 7/1995 | Lloyd et al. |
| 5,784,795 A | 7/1998 | Tinarelli |
| 6,040,853 A | 3/2000 | Delagnes et al. |
| 6,446,509 B1 | 9/2002 | Takada et al. |
| 6,940,295 B2 | 9/2005 | Engelbart et al. |

*Primary Examiner*—Robert R Raevis
(74) *Attorney, Agent, or Firm*—Lee & Hayes, PLLC

(57) ABSTRACT

Apparatus and methods for adjustably supporting probes are disclosed. In one embodiment, a sensor support assembly includes a base member adapted to be positioned proximate to and move along a surface of a material, the base member including a first outwardly projecting engagement member and a second outwardly projecting engagement member spaced apart from the first engagement member, and a support member coupled to the base member and including a boss adapted to engage a probe, wherein the first and second engagement members are adapted to engage the surface and to maintain a stand-off distance between the probe and the surface.

20 Claims, 9 Drawing Sheets

APPARATUS AND METHODS FOR ADJUSTABLY SUPPORTING PROBES

CROSS-REFERENCE TO RELATED APPLICATIONS

This patent application is a continuation-in-part of co-pending, commonly-owned U.S. patent application Ser. No. 11/183,203 entitled "Apparatus and Methods for Adjustably Supporting Probes" filed on Oct. 6, 2005, which application is incorporated herein by reference.

GOVERNMENT LICENSE RIGHTS

This invention was made with United States Government support under U.S. Government contract OSD01-CBMO5 PHASE II SBIR awarded by the Air Force Research Laboratory. The Government has certain rights in this invention.

FIELD OF THE INVENTION

This invention relates generally to apparatus and methods for surface inspection and, more specifically, to apparatus and methods for adjustably supporting probes during surface inspections.

BACKGROUND OF THE INVENTION

Detection and repair of corrosion is a major issue in the aging aircraft industry. An aircraft may spend months in a depot facility awaiting completion of inspection, disassembly, repair, replacement and reassembly operations. A significant portion of this downtime may be due to the unavailability of spare replacement parts, which are often ordered from the suppliers as the need arises. Because field-level inspections are often only visual, the real extent of possible corrosion may not be determined until depot-level inspections are performed. Improving the quality, reliability, and sensitivity of field-level inspections may make it possible to obtain improved data on the extent of possible corrosion and may anticipate the need for spare parts prior to arrival at the depot. Because depot inspections may be much more extensive than field operations, increasing the speed and area of coverage of these inspections would reduce aircraft downtime, as well as operational and maintenance costs.

SUMMARY

The present invention is directed to apparatus and methods for adjustably supporting probes during surface inspections. Embodiments of the present invention may advantageously maintain a desired stand-off distance between a motion platform and a surface to be inspected, even as a surface curvature is encountered during inspection. Embodiments of the present invention may also improve the reliability and sensitivity of field-level inspection instruments, and may improve the quality of the acquired inspection data.

In one embodiment, a sensor support assembly includes a base member adapted to be positioned proximate to and move along a surface of a material, the base member including a first outwardly projecting engagement member and a second outwardly projecting engagement member spaced apart from the first engagement member, and a support member coupled to the base member and including a boss adapted to engage a probe, wherein the first and second engagement members are adapted to engage the surface and to maintain a stand-off distance between the probe and the surface.

BRIEF DESCRIPTION OF THE DRAWINGS

Embodiments of the present invention are described in detail below with reference to the following drawings.

DETAILED DESCRIPTION

The present invention relates to apparatus and methods for adjustably supporting probes during surface inspections. Many specific details of certain embodiments of the invention are set forth in the following description and in FIGS. 1-12 to provide a thorough understanding of such embodiments. One skilled in the art, however, will understand that the present invention may have additional embodiments, or that the present invention may be practiced without several of the details described in the following description.

Figure 1:
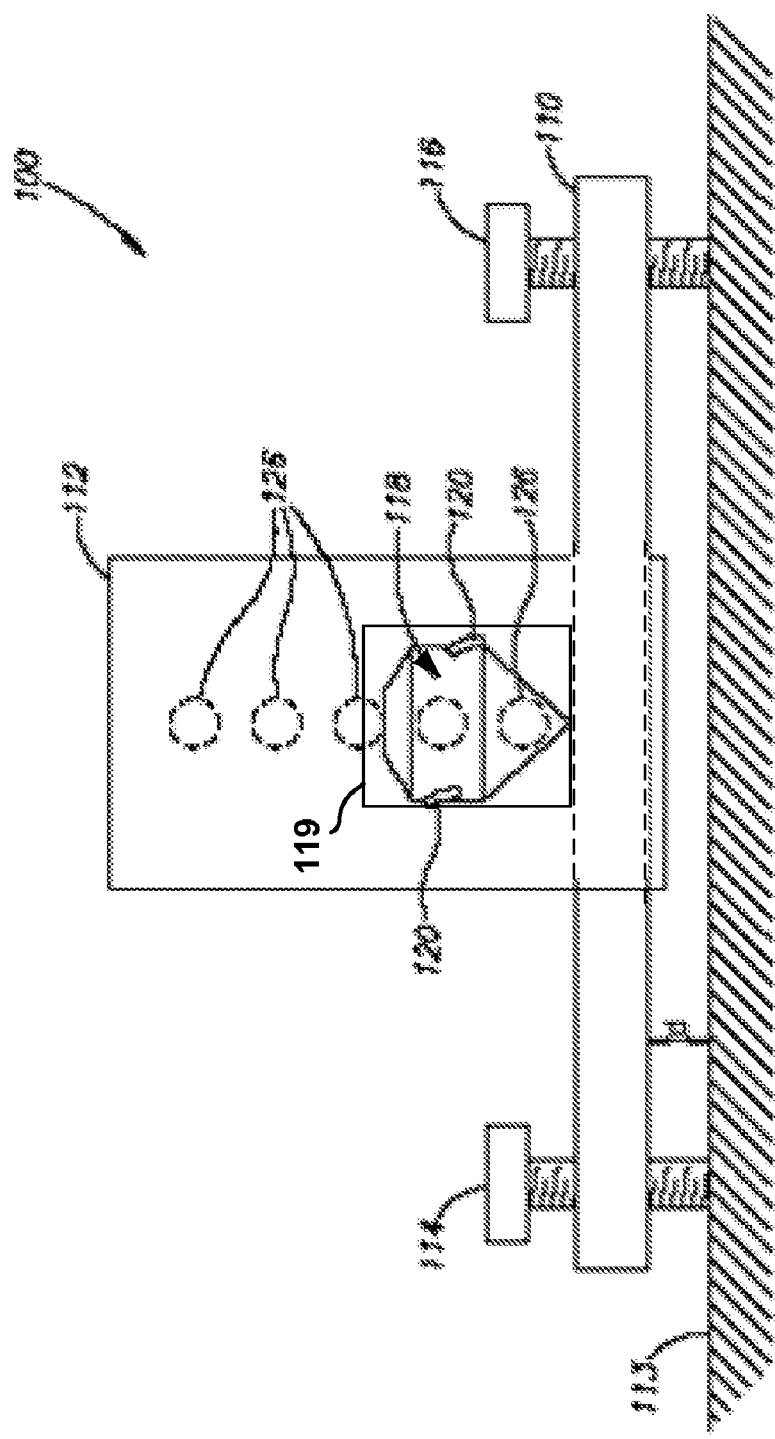
FIG. 1 is a front elevational view of a sensor support assembly for adjusting a motion platform to a surface according to an embodiment of the invention.
Figure 2A:
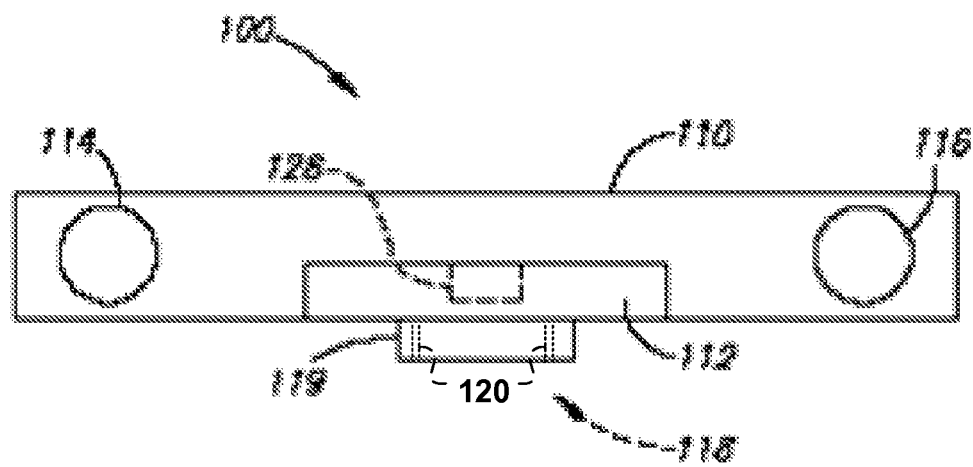
FIG. 2A is a top elevational view of the sensor support assembly of FIG. 1.
Figure 2B:
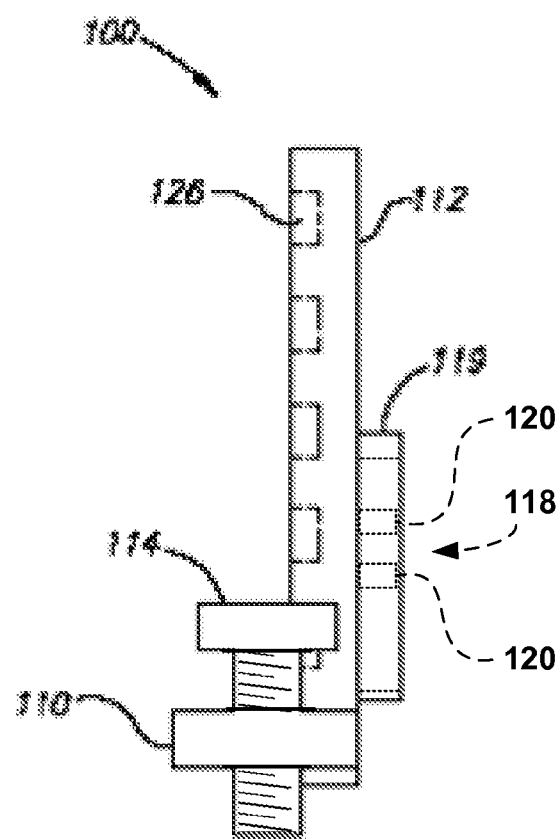
FIG. 2B is a side elevational view of the sensor support assembly of FIG. 1.

FIG. 1 is a front elevational view of a sensor support assembly 100 in accordance with an embodiment of the invention. FIGS. 2A and 2B are top and side elevational views, respectively, of the sensor support assembly 100 of FIG. 1. In this embodiment, the sensor support assembly 100 includes a base member 110 coupled to a support member 112. The base member 110 may be adapted to be positioned proximate to and move along a surface 113 of a component or material to be inspected. Suitable surfaces 113 may include aircraft fuselages, aircraft component surfaces, and any other surfaces that may require inspection.

As best shown in FIG. 1, the base member 110 includes a first engagement member 114 at a first end and a second engagement member 116 at a second end. The engagement members 114, 116 may be adapted to maintain a desired stand-off distance d between the base member 110 and the surface 113. In one embodiment, the engagement members 114, 116 may comprise threaded members that threadedly engage with the base member 110, allowing the stand-off distance d to be adjusted by simply rotating the engagement member 114, 116 a first direction to increase the stand-off distance d, and a second direction to decrease the stand-off distance d. As the term is used herein, the stand-off distance d refers to the distance between the base member 110 and the surface 113, however, it will be appreciated that the stand-off distance d may be used to refer to other components of the sensor support assembly 100 (including a sensor attached to the support member 112). In one particular embodiment, the stand-off distance d may be approximately even (or constant) across the entirety of the base member 110, however, in alternate embodiments, the stand-off distance d may vary from one end of the base member 110 to the other. The sensor support assembly 100 may be moved manually over the surface 113, or alternately, the sensor support assembly 100 may be coupled to a motion platform to perform scanning of the surface 113, as described more fully below.

The engagement members 114, 116 may be formed of any suitable material, including materials having a low coefficient of friction that enable the sensor support assembly 100 to be slid along the surface 113 with relative ease and without marking or damaging the surface 113, including, for example, nylon, fluoropolymer (e.g. Teflon®), or any other suitable materials. In one specific embodiment, the engagement members 114, 116 comprise nylon screws commercially-available from McMaster-Carr and having rounded ends that slideably engaged the surface 113.

As further shown in FIGS. 1, 2A, and 2B, the support member 112 includes a boss 118 formed therein and adapted to engage a probe or sensor (not shown) used, for example, to inspect the surface 113. In one particular embodiment, the boss 118 may be machined into a raised portion 119 (FIG. 2A) of the support member 112. Coupling members (e.g. clamps) 120 are provided to couple the probe (not shown) to the support member 112.

In this embodiment, the support member 112 also includes a plurality of apertures 126. The apertures 126 may be suitably sized to accommodate a plurality of fasteners (not shown) that threadably engage into the support member 112. Each aperture 126 may provide a point of attachment for attaching the support member 112 to a suitable motion platform (not shown in FIGS. 1, 2A, and 2B), as described more fully below (e.g. with respect to embodiments of motion platforms shown in FIGS. 3, 6A, 6B, and 10), and each fastener may provide a pivot point for pivotably moving the support member 112 with respect to the motion platform in order to accommodate a curvature of the surface 113 during motion of the motion platform along the surface 113. For example, the pivoting capability of the fastener may provide the motion platform with the ability to maintain its stand-off distance with the surface 113, even as the motion platform approaches a surface curvature. In one embodiment, the apertures 126 may be threaded apertures, and the fasteners may be threaded fasteners.

It will be appreciated that the sensor support assembly 100 may be used with a variety of inspection probes, including, for example, ultrasonic, mechanical and microwave probes. In one particular embodiment, the sensor support assembly 100 may be used to support a microwave probe employed as a nondestructive method of detecting moisture in honeycomb core materials without the use of radiography. The use of microwave sensors for nondestructive testing is described more fully, for example, in co-pending, commonly-owned U.S. patent application Ser. No. 10/459,957, which application is incorporated herein by reference. Because microwave technology may be sensitive to low levels of corrosion, such as pitting, a microwave probe may provide viable field and depot-level inspections for detecting early stages of corrosion.

Figure 3:
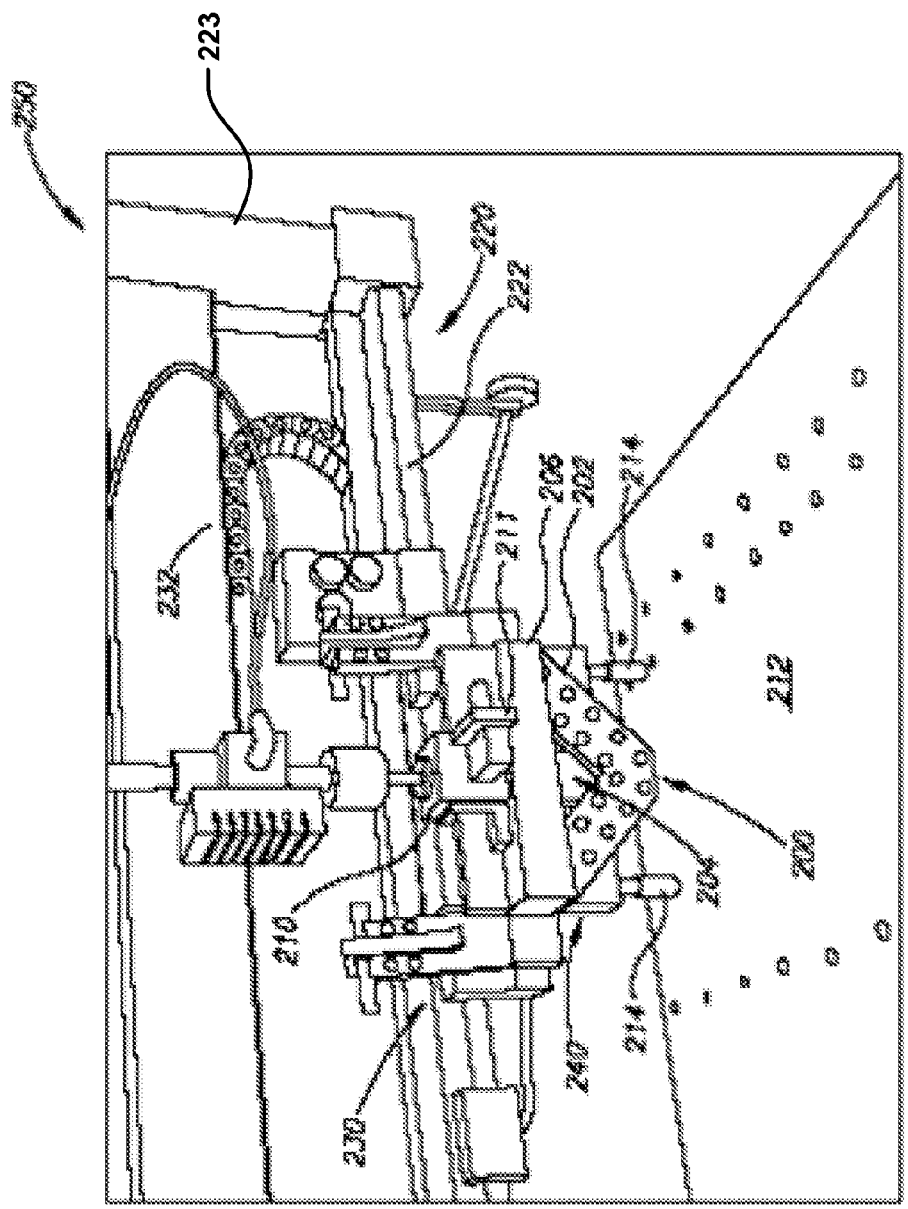
FIG. 3 is an isometric view of a test assembly in accordance with another embodiment of the invention.
Figure 4:
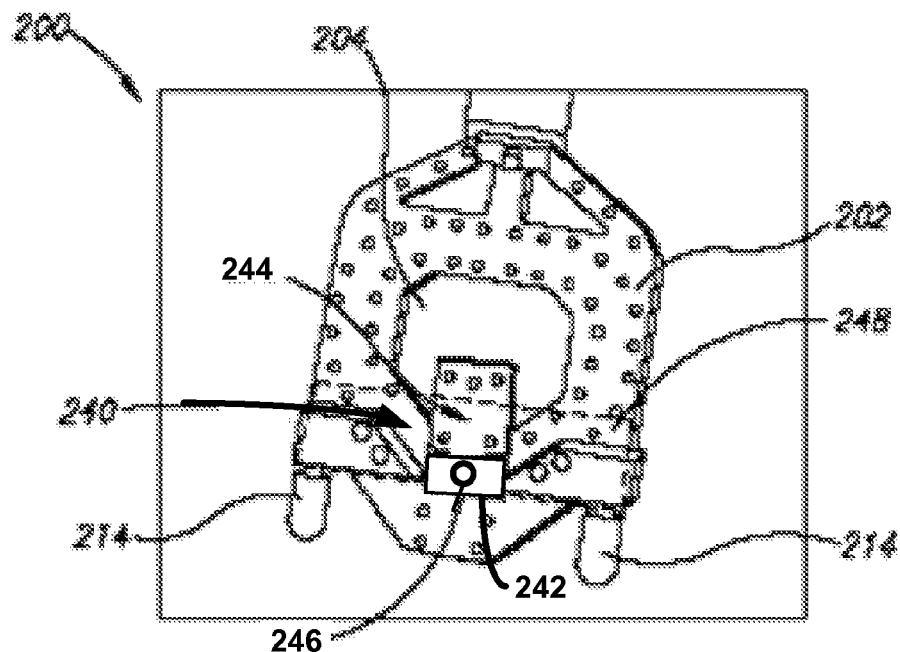
FIG. 4 is a back isometric view of a portion of a sensor assembly of FIG. 3.
Figure 5:
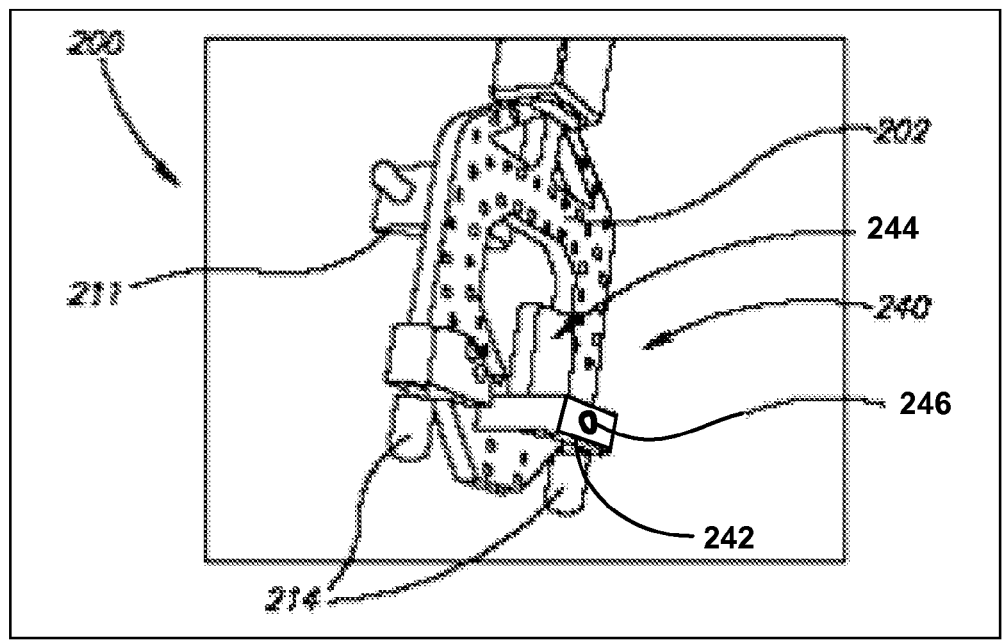
FIG. 5 is a side isometric view of a portion of a sensor assembly of FIG. 3.

FIG. 3 is an isometric view of a test assembly 250 that includes a sensor assembly 200 attached to a motion platform 220 in accordance with another embodiment of the invention. FIGS. 4 and 5 are partial isometric views of the sensor assembly 200 of FIG. 3 (with the sensor 210 removed). In this embodiment, the sensor assembly 200 includes a support plate 202 having an aperture 204 disposed therethrough. A horizontal member 206 (FIG. 3) is coupled to the support plate 202 and spans across the aperture 204. A sensor (or probe) 210 is coupled to the support plate 202 at a position above the horizontal member 206 by a mounting member 211. The sensor 210 is adapted to transmit signals onto a component under test 212 for performing non-destructive testing. A pair of adjustable engagement members 214 project outwardly from the support plate 202 toward the component under test 212. As described above, the engagement members 214 may be adapted to maintain a desired stand-off distance d between the sensor assembly 200 (i.e. the sensor 210) and the component under test 212.

In one embodiment, the motion platform 220 shown in FIG. 3 includes a support bar 222 mounted on a primary carriage assembly 223 that enables the support bar 222 to be positioned over the component under test 212. The sensor assembly 200 may be coupled to the support bar 222 by a secondary carriage assembly (or slide) 230. In the embodiment shown in FIG. 3, the secondary carriage assembly 230 is moveably coupled to the support bar 222, and a drive assembly 232 is coupled to the secondary carriage assembly 230 for driving the secondary carriage assembly 232 and the sensor assembly 200 along the support bar 222. In one particular embodiment, the drive assembly 232 includes a drive linkage (or drive chain) that is driven by an electric motor (not shown).

The motion platform 220 may, for example, comprise an automated, nondestructive inspection system for composite and bonded aerospace structures, although other testing and inspection devices may be suitable. In one particular embodiment, the motion platform 220 may comprise an Automated Ultrasonic Scanning System® (AUSS), commercially available from The Boeing Company of Chicago, Ill. In another embodiment, the motion platform 220 may comprise a Mobile Automated Scanner® (MAUS), also commercially available from The Boeing Company. It will be appreciated, however, that other automated ultrasonic and multi-mode nondestructive inspection systems of various configurations may also be suitable. In further embodiments, retrofit kits may be made available to upgrade existing apparatuses to provide for the new capability.

As further shown in FIGS. 4 and 5, the sensor assembly 200 further includes a coupling assembly 240 adapted to moveably couple the sensor assembly 200 to the motion platform 220. By moveably coupling the sensor assembly 200 to the motion platform 220, as described more fully below in the description of FIG. 7, the coupling assembly 240 enables the sensor assembly 200 to adjust its orientation (e.g. pitch and roll) as the engagement members 214 of the sensor assembly 200 are moved along a surface having curvature or non-uniformity, allowing the sensor 210 to maintain a more appropriate or desirable orientation with respect to the component under test 212. As described more fully above, each engagement member 214 may include a relatively low-friction portion adapted to slideably engage with the component under test 212.

Figure 6A:
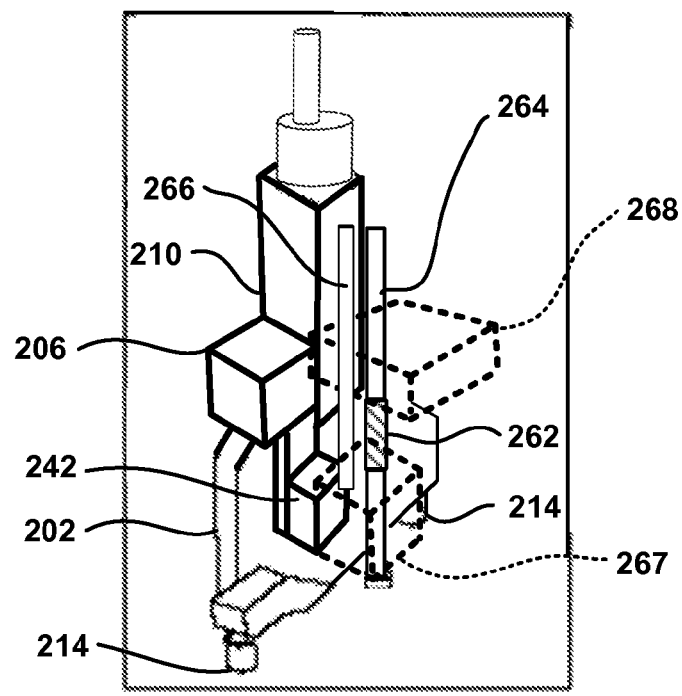
FIG. 6A is a partial side isometric view of a portion of the sensor assembly of FIG. 3.
Figure 6B:
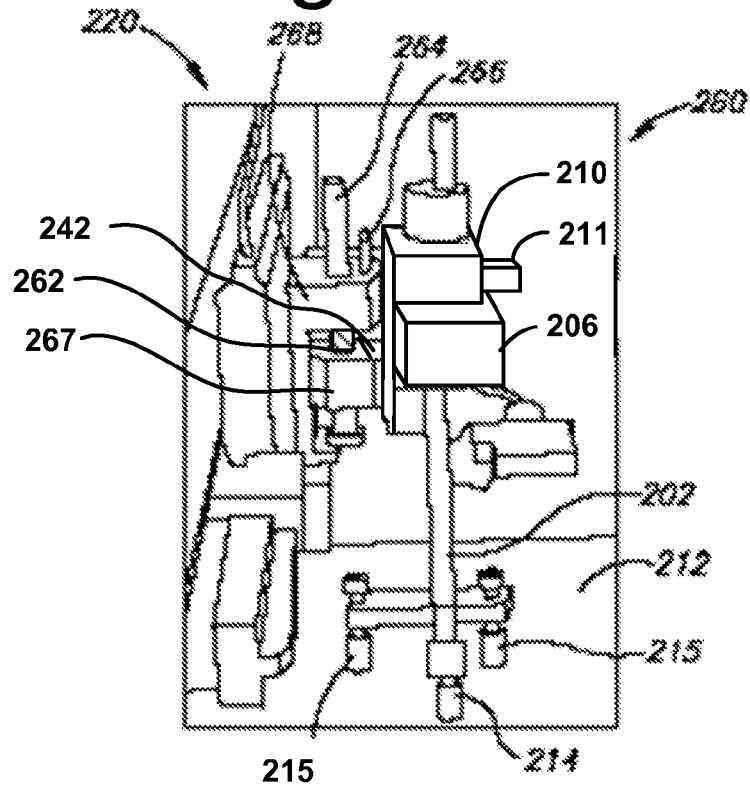
FIG. 6B is a side isometric view of a portion of the test assembly of FIG. 3.

FIG. 6A is a partial side isometric view of a portion of a sensor assembly 260 in accordance with an alternate embodiment of the invention, and FIG. 6B is a side isometric view of the sensor assembly 260 of FIG. 6A coupled to the motion platform 220 of FIG. 3. As shown in FIGS. 6A and 6B, in this embodiment, the sensor assembly 260 further includes a tension spring 262, a rod 264 and a guide rod 266. A large bracket 268 is coupled to the motion platform 220, and the rod 264 is attached to the large bracket 268. The tension spring 262 is disposed about the rod 264 and is contained between the large bracket 268 and a small bracket 267. In turn, the small bracket 267 is coupled to the sensor assembly 260, as described below with reference to FIG. 7. The tension spring 262 provides a biasing force that urges the small bracket 267, and thus the sensor 210, toward the component under test 212, and more specifically, urges the engagement members 214 (FIG. 6B) into contact with the component under test 212. A plurality of springs 262 with varying tensions may be employed, depending upon the desired pressure. The rod 264 runs through the spring 262 and supports the spring 262 as it moves in an upward and downward motion. A smaller guide rod 266 attaches to the small bracket 267 and slides through the large bracket 267. As further shown in FIG. 6B, the sensor assembly 260 may also include a pair of supplemental engagement members 215 coupled to the support plate 202 that engage with the component under test 212 and serve to maintain the standoff distance d, and the alignment of the sensor 210, over the component under test 212.

Figure 7:
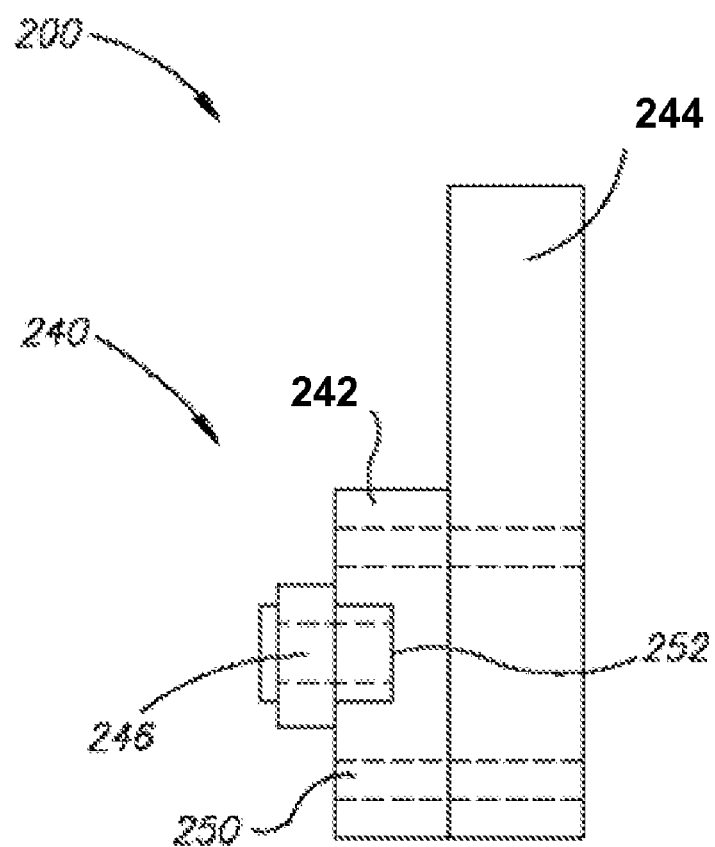
FIG. 7 is a side cross-sectional view of the coupling portion of the sensor assembly of FIGS. 4 and 5.

As described above, sensor assemblies in accordance with the present invention may be pivotable and rotatably coupled to the motion platform 220 so that as the sensor assembly is traversed over the component under test 212, the position of the sensor assembly automatically adjusts to the contours of the surface in order to maintain the desired standoff distance d, and the desired orientation of the sensor 210, over the component under test 212. More specifically, FIG. 7 is a side cross-sectional view of the coupling portion 240 of the sensor assembly 200 of FIGS. 4 and 5. With reference to FIGS. 4, 5, and 7, the coupling assembly 240 includes a mounting plate 242 that is adapted to attach the sensor assembly 200 to the secondary carriage assembly 230 or other portion of the motion platform 220. The mounting plate 242 is coupled to an angle bracket 244. In the illustrated embodiment, the mounting plate 242 is fastened to the angle bracket 244 by fasteners (not shown) disposed into fastener holes 250. The angle bracket 244 is coupled to the support plate 202 by a pivotable, rotatable attachment member 246. In one particular embodiment, the attachment member 246 is a bearing bolt that enables the angle bracket 244 to pivot in any direction with respect to the support plate 202, as well as to rotate (or roll) with respect to the support plate 202. In alternate embodiments, other attachment members 246 may be employed, including ball-and-socket attachments, or other attachments that provide less freedom of movement of the angle bracket 244 with respect to the support plate 202. In a further embodiment, the mounting plate 242 and the angle bracket 244 may be replaced with a flat strip 248 (shown in dotted lines in FIG. 4) that is simply coupled to the attachment member 246 and is, in turn, coupled to the motion platform 220 (e.g. to the secondary carriage assembly 230).

Figure 8:
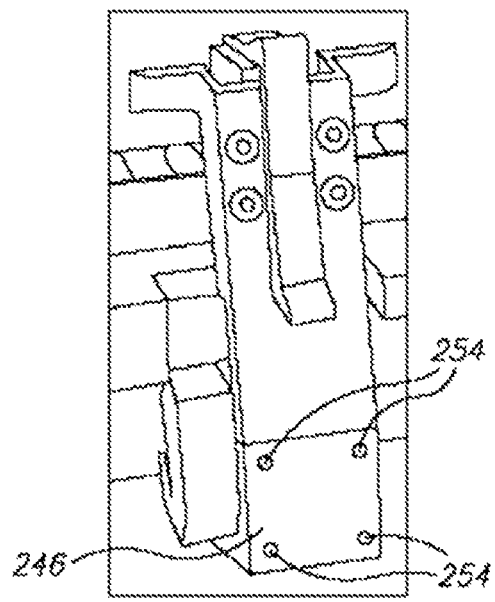
FIG. 8 is an isometric view of a MAUS bracket in accordance with an embodiment of the present invention.
Figure 9:
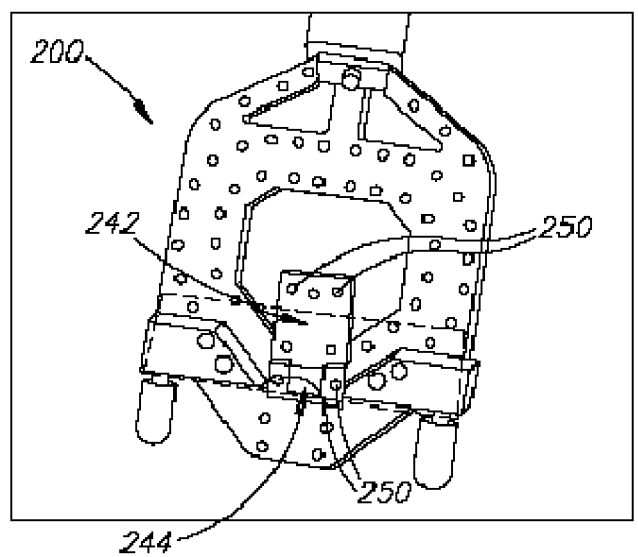
FIG. 9 is a back isometric view of the sensor assembly of FIGS. 3 through 5.

FIGS. 8 and 9 further illustrate the coupling assembly 240 of the sensor assembly 200. FIG. 9 is a back isometric view of a portion of the sensor assembly 200. Fastener holes 250 are located in the corner of the mounting plate 242 to correspond with the mounting location on the MAUS, or other sensor, as illustrated by FIG. 8. FIG. 8 shows the mounting locations 254 on the attachment member 246 that correspond to the fastener holes of the mounting plate on the sensor assembly.

Figure 10:
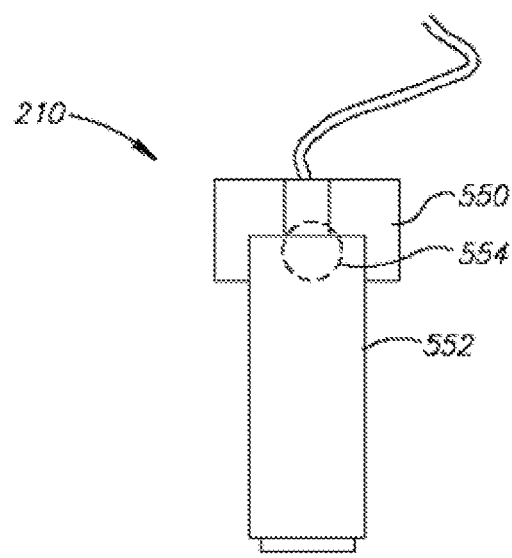
FIG. 10 is a side elevational view of a sensor of the sensor assembly of FIG. 3.

FIG. 10 is a side elevational view of the sensor 210 of the sensor assembly 200 of FIG. 3. In this embodiment, the sensor 210 includes a support base 550 coupled to a main body 552 and having a center of gravity 554. In one embodiment, the support plate 202 (FIGS. 3-5) is coupled to the support base 550 a location relatively low on the sensor 210 and proximate to the center of gravity 554 so as to prevent the sensor 210 from appreciably wobbling or titling during the inspection scanning process.

The sensor 210 may include a microwave sensor of generally-known construction and having principles of operation that are generally understood. In brief, the microwave sensor may transmit microwaves onto a workpiece, and reflected microwave signals are sensed by the microwave sensor. The reduction in the energy level between the transmitted microwaves and the reflected microwaves provides a measurement of the microwave energy absorbed by the workpiece. Post-processing of the energy absorption measurements, which may include accounting for variations in an intensity field of the incident microwaves, provides an estimate of the corrosion levels of the targeted portion of the workpiece. The microwave sensor and its related components may of any known type, including, for example, those sensor assemblies disclosed in U.S. Pat. No. 6,411,105 issued to Lui, and in U.S. Pat. No. 5,648,038 issued to Fathi et al., which patents are incorporated herein by reference, or may include any other suitable microwave sensor assemblies. In one embodiment, a microwave sensor assembly employs reflectometers having an open-ended rectangular waveguide that may operate in the Ka band (26.5 to 40 GHz). In alternate embodiments, the waveguide may operate in the V band (50 to 75 GHz), the U band (40 to 60 GHz), and the W band (75 to 110 GHz), or any other suitable range.

Figure 11:
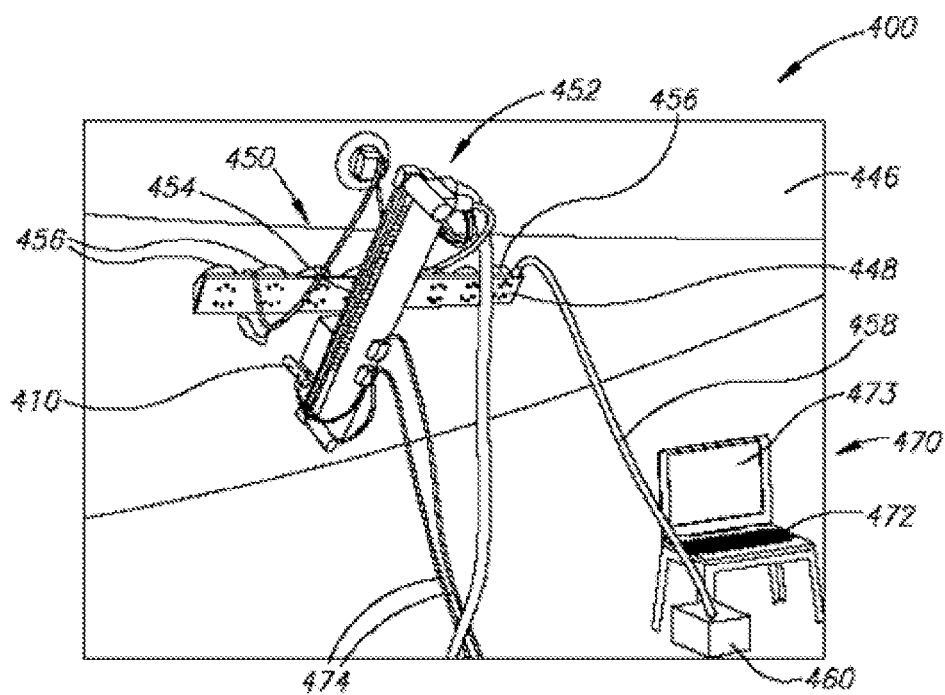
FIG. 11 is an isometric view of a test assembly coupled to a contoured surface in accordance with an alternate embodiment of the invention.

FIG. 11 is an isometric view of a test assembly 400 coupled to a contoured surface 446, in this case, an aircraft fuselage. The test assembly 400 includes a sensor assembly 410 coupled to a motion platform 450 that is removeably attached to the contoured surface 446. The test assembly 400 may be used to efficiently, accurately, and systematically scan the contoured surface 446 to provide an assessment of the amount of corrosion present in the aircraft fuselage.

More specifically, in this embodiment, the motion platform 450 includes a bar scanner 452 that is, in turn, attached to a track carriage 454. An elongated track 448 supports the track carriage 454 and is attachable to the contoured surface 446 by a plurality of vacuum cup assemblies 456. The vacuum cup assemblies 456 are fluidly coupled to one or more vacuum lines 458 leading to a vacuum source 460, such as a vacuum pump, air line, valve, or the like. It may be appreciated that the vacuum cup assemblies 456 are of known construction and may be of the type described, for example, in U.S. Pat. No. 6,467,385 B1 issued to Buttrick et al., or U.S. Pat. No. 6,210,084 B1 issued to Banks et al. The vacuum from the vacuum source 460 may be controllably applied to (and removed from) the vacuum cup assemblies 456 during, for example, mounting, re-positioning, and removal of the track 448 to and from the workpiece 446. In one particular embodiment, for example, to release the track 448, the vacuum source 460 or air line supply may be adjusted to allow for air flow under the vacuum cup assemblies 456. In alternate embodiments, the vacuum cup assemblies 456 may be replaced with other types of attachment assemblies, including magnetic attachment assemblies, bolts or other threaded attachment members, or any other suitable attachment assemblies. Furthermore, it may also be appreciated that the track 448 may be flexible to enable the track 448 to bend and twist to follow the surface of the contoured surface 446, or alternately, may be rigid.

As further shown in FIG. 11, the test assembly 400 has a control system 470 that includes a computer 472 coupled to the sensor assembly 410 and the motion platform 40 by one or more signal leads 474. The computer 472 may include a CPU and one or more memory devices that house software that may perform data acquisition, analysis, processing, and display functions. An output device 473, such as a display or a printer, is coupled to the computer 472 for outputting test results. It may be appreciated that the control system 470 may be a conventional control system, including, for example and not by way of limitation, the control system 470 of the above-referenced conventional test system known as the Mobile Automated Scanner (MAUS) commercially-available from The Boeing Company, of Chicago, Ill.

In operation, the motion platform 450 is coupled to the contoured surface 446 proximate an area to be inspected by applying vacuum to the vacuum assemblies 456. The sensor 210 of the sensor assembly 200 is activated, and appropriate control signals are transmitted by the control system 470 to the motion platform 450, which moves the sensor assembly 200 along the contoured surface 446. More specifically, the sensor assembly 200 may be moved along the length of the bar scanner 452, and the bar scanner 452 may be moved along the length of the track 448. These movements may be performed sequentially or simultaneously to inspect a desired portion of the contoured surface 446. The engagement members 214 provide a desired standoff distance d of the sensor 210 from the contoured surface 446, and the coupling assembly 240 that couples the sensor assembly 200 to the motion platform 450 enables the sensor assembly 200 to adjustably orient its position (e.g. pitch and roll) as the sensor assembly 200 slideably moves over the contoured surface 446.

Figure 12:
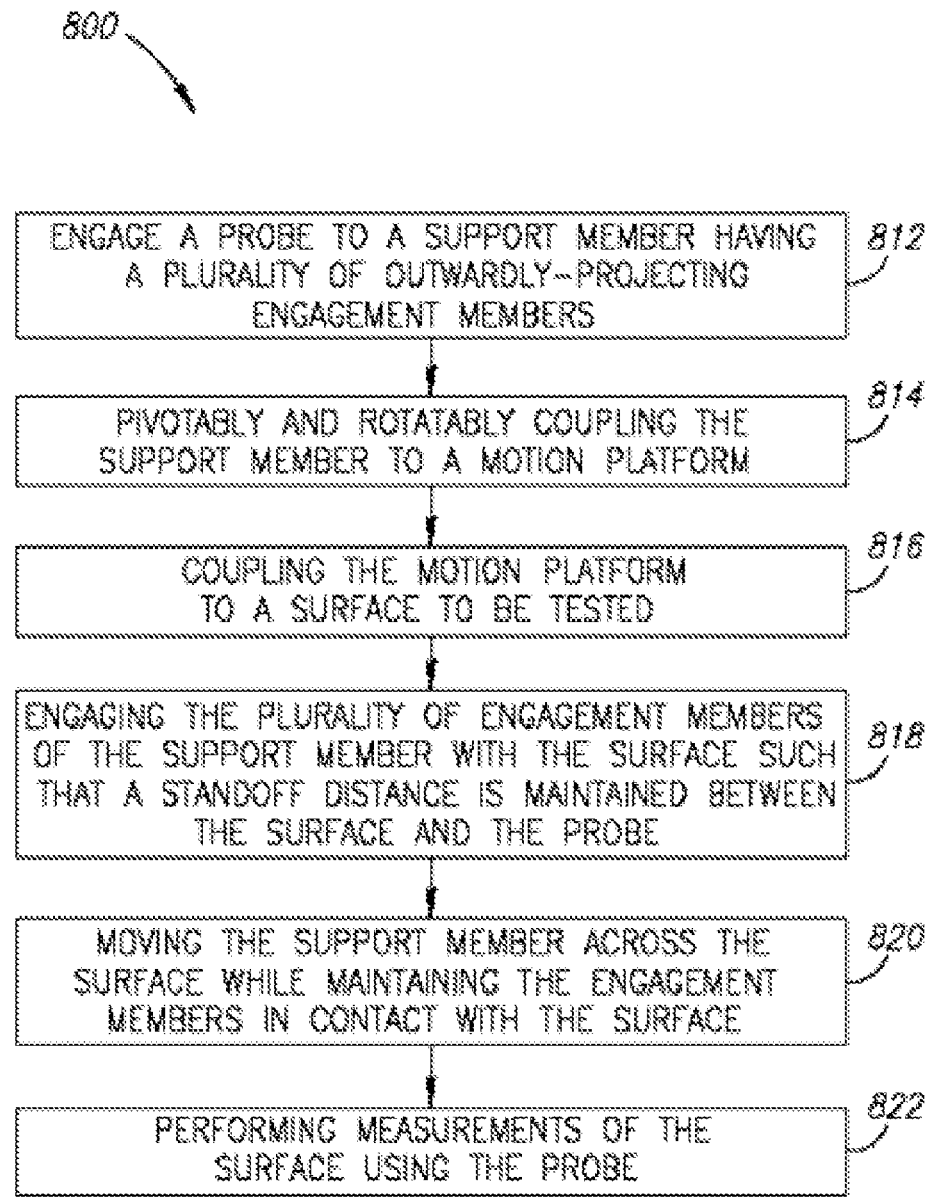
FIG. 12 is a block diagram of a method of performing an inspection of a surface in accordance with an embodiment of the invention.

FIG. 12 is a block diagram of a method 800 of performing an inspection of a surface in accordance with an embodiment of the invention. At a block 812, a probe is coupled to a support member having a plurality of outwardly-projecting engagement members. At a block 814, the support member is moveably coupled (e.g. pivotably and rotatably coupled) to a motion platform. At a block 816, the motion platform is coupled to the surface to be tested. The plurality of engagement members of the support member are then engaged with the surface at a block 818 such that a standoff distance is maintained between the surface and the probe. At a block 820, the support member is moved across the surface while maintaining the engagement members in contact with the surface. Finally, at a block 822, measurements of the surface are performed using the probe. The measurements (block 822) may be performed simultaneously or sequentially with the movement of the support member across the surface (block 820).

Embodiments of the present invention may provide improved performance of nondestructive inspection testing. For example, embodiments of the invention may provide enhanced and expanded capabilities of existing instrumentation, and may improve the quality of the acquired inspection data. Further, embodiments of the present invention may provide for earlier detection prior to aircraft arrival at the depot, and may also provide for possible anticipation and advanced preparation of needed repairs and replacement parts, significantly reducing aircraft downtime.

While preferred and alternate embodiments of the invention have been illustrated and described, as noted above, many changes can be made without departing from the spirit and scope of the invention. Accordingly, the scope of the invention is not limited by the disclosure of these preferred and alternate embodiments. Instead, the invention should be determined entirely by reference to the claims that follow.

What is claimed is:

1. A sensor support assembly configured to support a probe during movement of the probe relative to a workpiece, comprising:
   a base member configured to be positioned proximate to and move along a surface of the workpiece, the base member including a first outwardly projecting engagement member and a second outwardly projecting engagement member spaced apart from the first engagement member;
   a support member coupled to the base member and including a boss configured to engage the probe, wherein the first and second engagement members are configured to engage the surface and to maintain a stand-off distance between the probe and the surface, and wherein the base member and support member are further configured to move along the surface with the probe during movement of the probe relative to the workpiece; and
   a coupling assembly coupled to the support member and configured to be coupled to a motion platform such that as the probe is moved relative to the surface, the support member is rotatable with respect to the motion platform about a rotation axis that is at least approximately aligned with a direction of movement of the probe relative to the surface.

2. The assembly of claim 1, wherein the base member includes a base and wherein the engagement members comprise threaded members configured to threadedly engage the base to allow the stand-off distance to be adjusted by rotating the engagement member in at least one of a first direction to increase the stand-off distance and a second direction to decrease the stand-off distance.

3. The assembly of claim 2, wherein the first and second engagement members are further configured to maintain the stand-off distance at an approximately constant value as the base member is moved along the surface.

4. The assembly of claim 1, wherein the boss comprises a boss machined into a raised portion of the support member.

5. The assembly of claim 1, wherein the coupling assembly is further configured to enable the support member to pivot with respect to the motion platform as the engagement members move along the surface.

6. The assembly of claim 1, wherein the support member includes an aperture and the coupling assembly includes an attachment member disposed through the aperture and configured to engage the motion platform, the attachment member being further configured to enable the support member to pivot with respect to the motion platform as the engagement members move along the surface.

7. The assembly of claim 6, wherein the support member includes a plurality of apertures disposed therein.

8. The assembly of claim 1, further comprising a motion platform coupled to the coupling assembly, the support member being pivotably coupled to the motion platform by the coupling assembly to allow the support member to pivotably move to accommodate unevenness of the surface during motion of the motion platform.

9. The assembly of claim 1, wherein the probe comprises at least one of an ultrasonic probe, and a microwave probe.

10. An assembly, comprising:
    a sensor support including
       a support plate having an aperture disposed therein;
       a sensor coupled to the support plate, the sensor being configured to transmit signals onto the workpiece;

a pair of adjustable engagement members projecting from the support plate toward the component, the adjustable members being configured to maintain a stand-off distance between the sensor and the workpiece as the sensor support is moved over a surface of the workpiece;

a motion platform operatively coupled to the sensor support and configured to controllably move the sensor support over at least a portion of the workpiece; and a coupling assembly coupled between the sensor support and the motion platform and configured such that as the sensor support is moved over the surface of the workpiece, the sensor support is rotatable with respect to the motion platform about a rotation axis that is at least approximately aligned with a direction of movement of the sensor support relative to the surface.

11. The assembly of claim 10, wherein the motion platform includes a carriage assembly operatively coupled to the sensor support and configured to controllably move the sensor support assembly over at least a portion of the component.

12. The assembly of claim 11, wherein the motion platform further includes a drive assembly coupled to the carriage assembly and configured to drive the carriage assembly along at least a first direction relative to the component.

13. The assembly of claim 10, wherein the coupling assembly is further configured to enable the sensor support to pivot with respect to the motion platform as the engagement members move along the surface.

14. The assembly of claim 10, wherein the sensor support includes an angle bracket coupled to the support plate by a pivotable rotatable attachment member.

15. The assembly of claim 10, wherein the sensor is coupled to the support plate at a location proximate to the center of gravity of the sensor.

16. The assembly of claim 10, wherein the motion platform includes a bar scanner attached to a track carriage supported by an elongated track attachable to a surface by a plurality of vacuum cup assemblies, the vacuum cup assemblies configured to perform at least one of mounting, positioning and removing the track.

17. The assembly of claim 10, further comprising a control system, including a computer coupled to the sensor assembly and the motion platform by at least one signal lead, configured to perform at least one of data acquisition, analysis, processing and display.

18. A method of inspecting a surface, comprising:

coupling a probe to a support member having a plurality of outwardly projecting engagement members;

pivotably and rotatably coupling the support member to a motion platform such that as the support member is moved relative to the surface by the motion platform, the support member is rotatable with respect to the motion platform about a rotation axis that is at least approximately aligned with a direction of movement of the support member relative to the surface;

engaging the plurality of engagement members with the surface such that a standoff distance is maintained between the probe and the surface;

moving the support member across the surface using the motion platform while maintaining the engagement members in contact with the surface;

simultaneously with moving the support member, at least one of pivoting and rotating the support member with respect to the motion platform; and performing measurements of the surface using the probe.

19. The method of claim 18, further comprising coupling the motion platform to at least one of the surface under test and a support surface.

20. The method of claim 18, wherein performing measurements of the surface includes performing measurements simultaneously with moving the support member across the surface.

* * * * *